United States Patent [19]

Cunningham

[11] 4,108,052
[45] Aug. 22, 1978

[54] APPARATUS FOR PRODUCING ALCOHOL FROM GRAINS OF STARCH MATERIALS

[76] Inventor: Newton T. Cunningham, 1324 Garfield Ave., Wyomissing, Pa. 19610

[21] Appl. No.: 789,702

[22] Filed: Apr. 21, 1977

Related U.S. Application Data

[63] Continuation-in-part of Ser. No. 637,865, Dec. 4, 1975, Pat. No. 4,035,515.

[51] Int. Cl.² .................. A23L 1/00; C12C 11/00
[52] U.S. Cl. ........................... 99/275; 99/358; 426/244
[58] Field of Search .................. 99/275–277.1, 99/358; 426/11, 12–14, 29, 237, 239, 244, 247; 219/284, 285

[56] References Cited

U.S. PATENT DOCUMENTS

| | | | |
|---|---|---|---|
| 3,468,240 | 9/1969 | Huppmann | 99/276 |
| 3,877,360 | 4/1975 | Vigerstrom | 99/358 |

*Primary Examiner*—Leonard D. Christian
*Attorney, Agent, or Firm*—D. Paul Weaver

[57] ABSTRACT

A new and improved process and apparatus for producing alcohol from cereal grains or starch materials is disclosed. The process involves cooking or mashing very rapidly by electric means to prevent any form of hydrolysis of the starch prior to enzymatic hydrolysis by malt. Specific over-all process steps include milling of the grain in a manner to improve the wetting of the grain; electric cooking or mashing; malting of the mash; fermentation and recovery by distillation. The apparatus principally comprises an electric cooking or mashing unit having a central electrode positioned within an electrically conductive outer wall with a suitable electric power source being provided across the central electrode and conductive wall. In accordance with the invention the mash is heated to a predetermined temperature in a matter of seconds without the addition of condensate. The cooking operation in this manner comprises a continuous flow system with the gelled mash being discharged at a continuous and predetermined rate. The process and apparatus of the invention overcome substantial difficulties of known industrial processes including an increase of normally accepted yields to yields near the theoretical.

4 Claims, 2 Drawing Figures

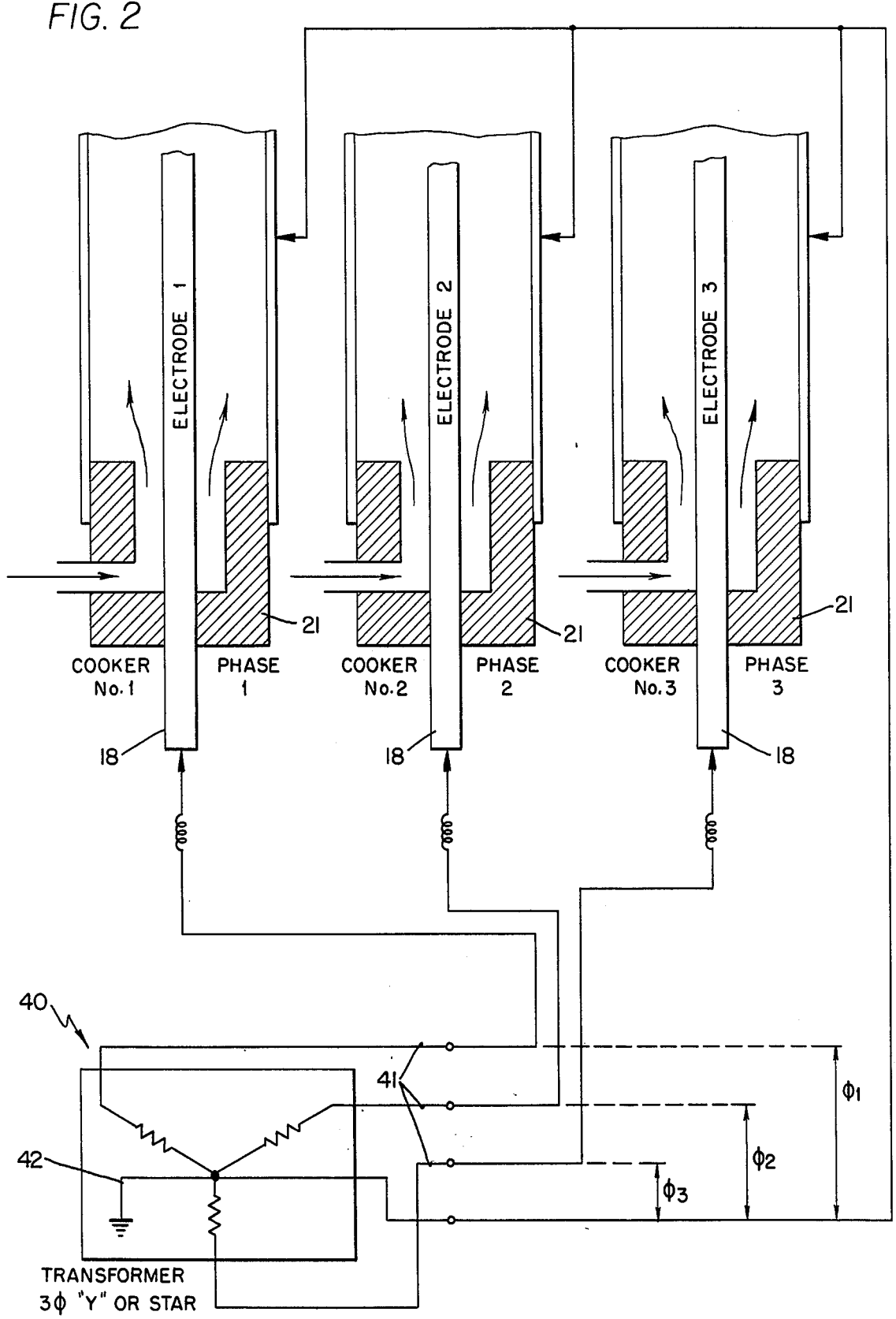

APPARATUS FOR PRODUCING ALCOHOL FROM GRAINS OF STARCH MATERIALS

RELATIONSHIP TO CO-PENDING APPLICATION

This present application is a continuation-in-part of U.S. Ser. No. 637,865, filed Dec. 4, 1975, now allowed as U.S. Pat. No. 4,035,515.

BACKGROUND OF THE INVENTION

1. Field of the Invention

The present invention relates to the production of alcohol and, more particularly, to a unique and improved apparatus for producing ethyl alcohol from cereal grains and like materials.

2. Description of the Prior Art

As is known in the art, commercial processes or techniques for producing ethyl alcohol from sugars involves the fermentation of glucose, the latter being in turn derived from starch or molasses. If molasses is employed no preparatory treatment is required. For grains such as, e.g., corn, wheat, rice, etc., it is necessary to convert the starch into glucose. In accordance with a process known as malting (converting starch to glucose), barley is steeped in water and allowed to germinate. During germination, an enzyme, diastase, is developed. The germinated barley is dried (malt) and when added to starch suspensions from grains converts the starch into maltose:

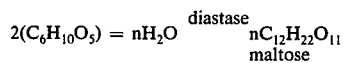

$$2(C_6H_{10}O_5) = nH_2O \xrightarrow{\text{diastase}} nC_{12}H_{22}O_{11}$$
$$\text{maltose}$$

Maltase, an enzyme produced by yeast, converts maltose to glucose. The glucose is decomposed to ethyl alcohol and carbon dioxide by the action of the enzyme zymase. With active yeast, the fermentation may be complete in two-three days. The alcohol is recovered from the fermentated solution by fractional distillation.

It has been stated that the fermentation of alcohol is as old as the yeast that causes it, with alcohol, in the form of wines, beer and spirits, being, for all practical purposes, prehistoric. Perhaps because of this fact, tradition still plays a large part in processes or techniques used for producing ethyl alcohol from cereal grains. This is true, notwithstanding the commercial significance of this industry. It should be apparent that modern thinking and technology should be employed where possible and it is this end to which the present invention is directed.

In this regard and again broadly speaking for the moment, conventional process steps involved in the fermentation of alcohol from cereal grains include: (1) milling of the grain; (2) mashing or cooking; (3) malting; (4) fermentation; and (5) distillation. Although various known apparatus and procedures are presently employed for carrying out each of the above steps or operations, in many instances little concern has been shown for their inherent disadvantages, nor have attempts been made, at least to the knowledge of the present inventor, to investigate certain basic concepts upon which each is based. For example, in milling, three basic types of apparatus are employed. These include the hammer mill, the attrition mill and the roller mill. All three types, however, have been found to leave portions of the grain as sharp, hard particles which results in significant time and energy (as heat) being required for the proper wetting of the grain with water to produce complete hydration.

In conventional operations the preparation of the mash (step 2) generally involves: (a) mixing the milled grain with water; (b) preparing the starch by heating or cooking; and (c) cooling. Most of the variables are to be found in the manipulation of time and temperature involved in the cooking. Three general combinations of the above principals are commonly followed. These include:

(1) Mixing the grain and water at low temperature, and step-wise elevating the temperature. Malting is done at any time in the process before the cook reaches top temperature;

(2) Mixing the grain and water at a desired temperature then raising the temperature and cooling to the malting temperature; and, (3) Mixing the grain and water at a desired temperature, holding to liquefy the starch, and then cooking to boiling, or, under pressure, cooling to malting temperature.

When using the first method (1), malting is usually done early in the process. The process can produce undesirable hydrolytic products of starch and leave raw or unconverted starch in the mash. In method (2), the object is to heat the mash for gelling the starch and sterilization before malting. In many instances the heating is done step-wise to permit liquefying of the starch prior to the formation of the gell or reaching the boiling point. If liquefaction is not effected, the mash becomes very thick, requiring much power for stirring and cooling. If liquefaction is done, alteration of the starch is inherent with the liquefication, thus changing the malt substrate. The third technique (3) involves the preparation of a grain slurry which is held for a scheduled time prior to boiling or pressure cooking. This method is the most severe on the starch, presenting the greatest chance for alteration of the starch by enzymes, excessive heat and inappropriate use of time.

As previously noted, the use of malt for converting the grain starch to usable yeast food (glucose) is dependent on diastatic enzymes. These enzymes are water soluble and are extractable from the ground malt. Here, the customary practice is to mill the malt to a fine powder, suspend the powder in about two pounds of water per pound of malt, and add the slurry to the main mash. If the malt is added to an ungelled mash, the temperatures are usually low, permitting full play of the enzymes during step-wise elevation of temperature. If added to a gelled mash, the malt slurry is added at about 140° F., held at that temperature for the desired time and then cooled. In all cases, it is necessary that care be taken to leave substantial amounts of diastase in the finished mash. This is necessary because in known processes not all the starch is converted before delivery to the fermenter. In the fermenter there is sufficient time for residual diastase to complete its work.

In conventional mashing process, the end product is maltose (a disaccharide). This the yeast does not use directly, but has its own enzyme (maltase) which splits the maltose into two molecules of glucose. In general, the time required to hydrolyze all of the starch to sugars is too great to be economical (a process often requiring many hours). The usual practice is to make sure that a very large amount of diastase acts slowly at fermenter temperatures so as to remove all of the starch in the course of a normal fermentation. A mash from grain, however, will carry many types of organisms, which may flourish on the mash, producing undesirable by-products and acid. Excess acidity not only slows the action of the yeast but represents a significant amount of yeast food.

The stripping of the alcohol from a fermented mash or beer is a standard operation founded on the physics of boiling mixtures. This operation generally presents no problem except that the steam condensate dilutes the residue or "stillage." The residue of grain after fermentation is valuable. Any unnecessary addition of water is therefore an added expense.

While many of the above problems or concepts of traditional distilling operations are art recognized, their disadvantages remain. The present invention is directed to their solution and the application of modern technology to the art of producing ethyl alcohol from grains or like materials.

SUMMARY OF THE INVENTION

In summary, the present invention relates to the production of alcohol from cereal grains or starch materials wherein the cooking or so-called mashing of the grain is effected very rapidly. In its broadest aspect, the invention embodies the concept of cooking (or hydrating) the grain in the shortest possible time to prevent any form of hydrolysis of the starch before enzymatic hydrolysis (by malt) begins. The invention is based, in part, on the discovery that undesirable forms of hydrolysis may be substantially reduced and eliminated, with the cooking or mashing operation being carried out in a very short time, i.e., on the order of less than 3 minutes, by cooking or heating the mash electrically. The basic theory underlying the invention may be expressed as follows: (1) the grain must be milled in such a fashion that all parts of the grain are wetted rapidly without lumping or balling; (2) once wet, the grain must be cooked or hydrated in the shortest possible time; and, (3) malting should be started immediately to prevent any undesirable hydrolysis.

In the development of the invention it was noted that a grain slurry was a conductor of electricity and that the passage of a current through a slurry delivered heat thereto at an efficiency of 90 to 95% of the current used. Thus, a mash may be heated to a predetermined temperature in a matter of seconds, depending on the quantities of liquid and the current density, without the addition of condensate. The cooking operation in this manner comprises a continuous flow system with the gelled mash being discharged at a predetermined and very rapid cooking rate. The electric cooking or mashing apparatus of the invention comprises a central electrode positioned within a cylindrical outer conduit or wall with means being provided for passing an electric current through the grain slurry to be heated.

From the above, it will be seen that the present invention relates to a novel process and apparatus for producing ethyl alcohol from starch which process overcomes substantial difficulties facing the prior art. The process of the invention includes the over-all basic combination of steps of the prior art, i.e., milling of the grain; mashing; malting; fermentation; and distillation, but also comprises certain novel techniques for effecting such steps. A remarkable aspect of the invention lies in the discovery that nominally accepted yields (on the order of 5.0 to 5.2 proof gallons per bushel grain) of the industry can be increased by the practice of the invention to that near the theoretical, i.e., as high as 5.7 to 5.8 proof gallons alcohol per bushel grain.

It is accordingly a general object of the present invention to provide a novel method and apparatus for producing ethyl alcohol from cereal grains or like materials, which method is not subject to the disadvantages of the prior art.

Another and more particular object is to provide a process for producing alcohol from cereal grains wherein the yields of alcohol per bushel of grain approximate that of the theoretical.

Yet another object is to provide a continuous method and apparatus for heating a grain-water slurry to form a gelled mass thereof.

A further object is to provide a method for producing ethyl alcohol from cereal grains or starch materials wherein the cooking or mashing of the grain is effected very rapidly to prevent any form of hydrolysis of the starch before enzymatic hydrolysis (by malt) begins.

BRIEF DESCRIPTION OF THE DRAWINGS

The manner in which the foregoing and other objects are achieved in accordance with the present invention will be better understood in view of the following detailed description and accompanying drawing wherein:

FIG. 2 is a schematic illustration, shown in elevation, of a suitable arrangement of apparatus for carrying out the invention which includes a plurality of cooking units, the figure further showing a particularly advantageous wiring diagram for the cookers, each on a phase and each phase grounded.

DESCRIPTION OF PREFERRED EMBODIMENT(S)

Figure 1:
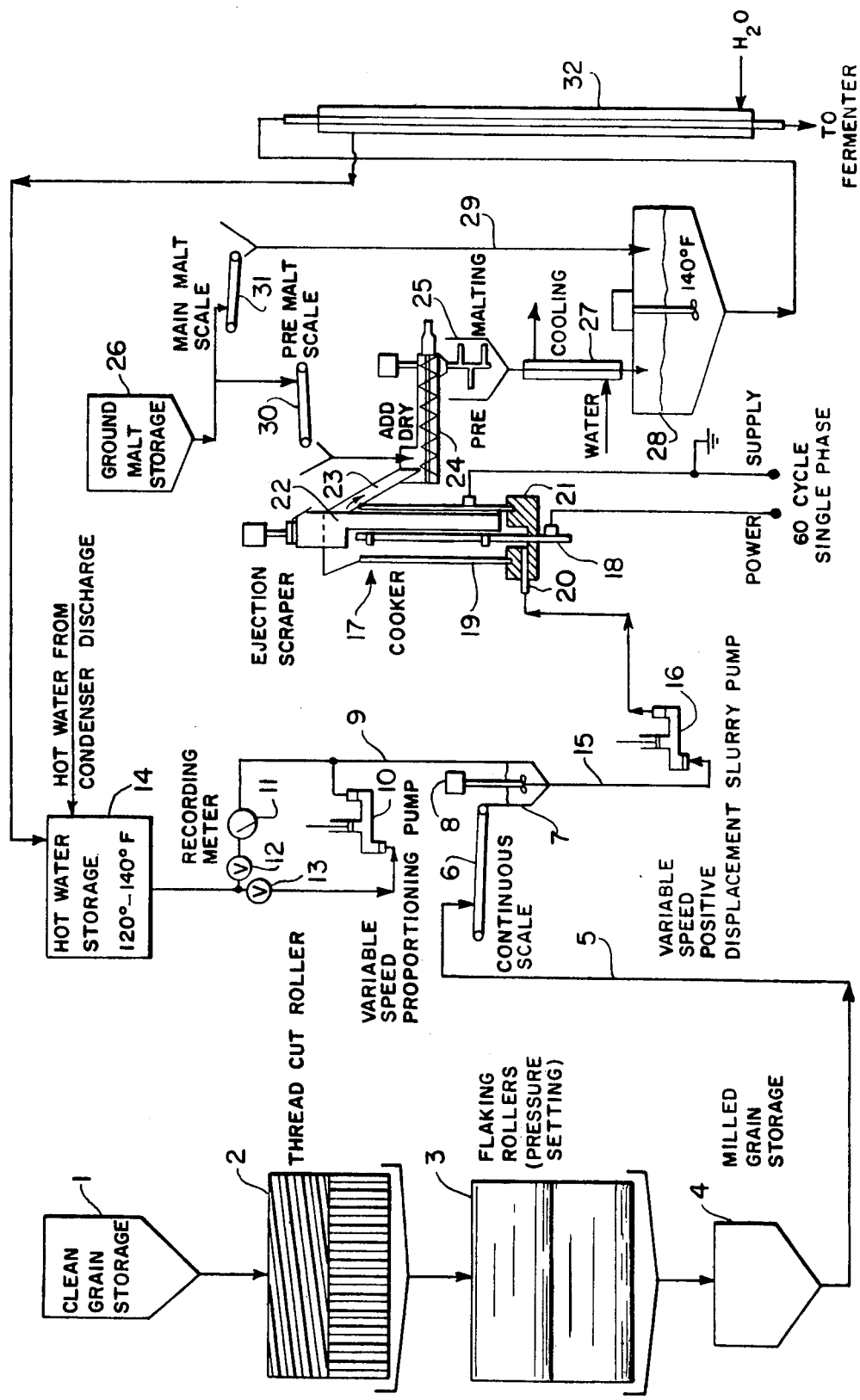
FIG. 1 is a schematic illustration, shown in elevation, of a suitable arrangement of apparatus for carrying out a particularly advantageous and preferred method embodiment of the invention.

As discussed above, the present invention is directed to a novel process and apparatus for producing alcohol wherein the mashing or cooking of the grain is effected very rapidly by passing an electric current through a slurry of the milled grain. In accordance with the invention enzymatic hydrolysis other than that produced by the malt is prevented and the yield of alcohol per bushel of grain is increased to that near or at the theoretical.

In this regard and to more fully understand the theory and practice of the invention, it may be noted at this point that starch is a carbohydrate composed of a large but indefinite number of hexose sugar molecules. It is believed that these hexoses are first combined to form a disacharide, the disacharide then condensed or dehydrated into successively larger groupings until the molecule becomes large enough to assume the behavior of starch. This complicated chemical synthesis apparently takes place in the plant under the influence of a set of enzymes common to all starch producing plants. When two molecules of the hexose (glucose) are joined by dehydration, the compound "maltose" is formed. Maltose is a disacharide. This sugar, maltose, appears in the formation of starch and then reappears in the hydrolysis of starch, being the most significant sugar produced by the enzymes of malt.

The chemical breakdown or hydrolysis of starch may be performed in several different ways. It is susceptible to hydrolysis under the influence of heat, acid, certain salts, and a variety of enzymes. Each method produces its own characteristic set of hydrolytic products as the process breaks up the groups of hexoses. The hydrolysis is complex and affected by many outside conditions. It therefore does not necessarily proceed in strict conformance to a single rule. Thus an hydrolysis performed by acid may not necessarily produce the same intermediates as one using enzymes as the hydrating agent. However, the final result of an hydrolysis of starch, regardless of method, will always be glucose. When performed by acids, heat, and certain other materials, the path of hydrolysis leads through a group of dextrines, a group of still lower compounds and then a final product glucose.

When malt is used, apparently much of the dextrine stage is avoided and the disacharide maltose appears as the dominant sugar. Further hydrolysis produces glucose from the maltose.

As the term implies, the hydrolysis of starch uses water in the reactions. Furthermore, starch is a "water loving" colloid. At temperatures of about 85° C. (186° F.) the starch molecule adsorbs large amounts of water accompanied by a swelling. The water is held physically (adsorbed) and has not yet entered into chemical reaction. By definition the starch has gelled, because it has turned from a powder to a paste which will set to a stiff moist semi-solid or gell. This physically held water is readily available for hydrolytic reactions when the proper conditions occur.

In relation to the hydrolysis of starch, it should be pointed out that most cereals carry a set of enzymes which will act on starch under conditions of heat and water prior to gelling. Thus a slurry of corn in water can be heated and held at temperature permitting these enzymes to work before the gelling temperature is reached. In so doing, sufficient starch may be altered that gelling will not take place when the slurry is boiled. It has been observed in the distillery that mashes, using this method of controlling the stiffness of a cooked grain, have a tendency to leave unconverted dextrines in the fermented mash or "beer." This is apparently due to the formation of significant amounts of hydrolytic products incapable of being reduced to maltose by the diastatic enzymes of malt.

As noted above, barley has the power to generate large quantities of the enzyme diastase. As used herein, the expression "malt" (unless otherwise specified) is defined as a sprouted and dried barley. The malt is usually milled to a powder and applied to a cooked starch as a water slurry thereof. In the practice of the invention, however, it is preferably used as a dry powder with no apparent loss of activity.

The principal function of malt is the conversion of starch to sugars usable by yeast. A hot, stiff gell, however, may be liquefied to a workable fluid by the addition of a very small amount of dry malt. The malt used in this fashion is killed by the high temperature. In connection with the hydrolysis of starch by diastase from malt, it should also be noted that if the starch is gelled with a minimum of heat and time, the sacharification, when followed by the iodine test, shows very little of the browns of dextrines. In the distilling industry it has been found that if a mash is partly sacharified (hydrolized) by the so-called liquefying enzymes, high temperature or long cooking periods, the iodine test indicates significant quantities of dextrines. During fermentation these dextrines appear very difficult for residual diastase to hydrolize to maltose. Such mashes are low in alcohol yield, and carry considerable unfermented materials quite similar to the dextrines.

In summary of the above, it may be stated:
1. Starch is the basic material from which alcohol is made by fermentation. The higher the starch content the higher the alcohol yield.
2. Starch, being unusable directly as a yeast food, must be converted or hydrolyzed to its basic hexose components before fermentation can take place.
3. The diastatic enzymes of malt are an efficient converter of starch to yeast food.
4. The hydration of starch by cooking to the gelling temperature speeds the hydrolysis by the enzymes of malt.
5. The malt enzymes are selective in their action and must be supplied with an unhydrolyzed starch to obtain high efficiency.
6. The hydrolysis of starch by means other than by the diastase of malt produces hydrolytic products unacceptable as a malt substrate.
7. Since cereal grains carry starch-splitting enzymes other than the diastase of malt, care must be taken to avoid the hydrolytic products of these enzymes if malt is to be used later in the process.

In considering the prior art, heating or cooking with steam have apparent drawbacks which defeat the requirements of the theory. The difficulties of the introduction of condensate and the handling of the gelled mash (still gells must be processed immediately) approach the undesirable effects of unwanted enzymatic action. In the discovery of the instant invention, it was first found that a grain slurry was a conductor of electricity and that the passage of an alternating current through a slurry delivered heat to the slurry at an efficiency of 90 to 95% of the current or wattage used. Thus a mash could be heated to a predetermined temperature in a matter of seconds, depending on the quantities of liquid and the current density, without the addition of condensate. The process comprises a flow-through process with the gelled mash being discharged at a predetermined cooking rate.

With the above in mind and turning now to more specific details of the invention, FIG. 1 is a schematic illustration of a particularly advantageous combination of apparatus employed in accordance with the present invention. Grain, such as corn, which has been cleaned by suitable separation means (not shown) is first passed to a grain storage vessel, indicated at 1. It should be noted that the milling process may include the "tempering" of the grain (a process of conditioning the grain with water), with the storage bin 1 being sized to accommodate a grain supply equal to the time of the tempering process. From the storage vessel 1 the grain is passed, as by gravity, to a dicing roller 2 wherein the kernels of the grain are cut or diced and broken into small fragments. The precise design of the dicing roller 2 is well known in the art and is only important from the standpoint that the kernels are properly cut. Dicing rollers having corrugations with thread cuts at not less than about 8 and up cuts per inch made at ¾ inch per foot spiral and run at 2-½ to 1 differential are satisfactory for this purpose and are, therefore, preferred. However, as aforesaid, such designs are well known with the specific details of the corrugations, etc., being routinely determinable for a given end result. The diced grain is then passed through flaking rolls 3 which have smooth surfaces, which further crush, mash and/or flake the kernels of the grain. A modification of the flaking roll known as the crimping roll may also be used. The crimping operation however requires higher moisture content and may require tempering. Again, it should be appreciated that the invention lies in recognition of the problem as to the need for improving the wetting characteristics of the grain and to properly mill same so as to achieve this result, and not in the design of the flaking or crimping rollers per se. For example, the size of the rollers is only dependent upon the production or throughput requirements.

From the rollers 3, the milled crimped or flaked grain is passed into a storage vessel 4. If the process is operated on a continuous basis, the milled grain is continuously withdrawn from the storage vessel 4 and passed through a conduit 5 onto a scale or weight belt indicated at 6. The continuous type of scale illustrated in the drawing is preferable to a volumetric feeding device because of possible variations in the flaking operations changing the specific gravity of the milled grain. From the belt 6, the milled grain is passed into a grain slurry make-up tank 7 provided with suitable mixing means 8 with the water being introduced by way of conduit 9. As shown in the drawing, a variable speed proportioning pump 10, a recording meter 11 and suitable control valves 12 and 13 may be provided so as to insure accurate control of the amount of water used to make up the grain slurry with the weight of the grain being set or controlled by the scale 6. In this regard, the addition of excess water should be avoided and the volume to which a bushel of grain is to be made up should be predetermined. As known in the art, when milled grain is added to water, one bushel will occupy an average of about 3.7 gallons of volume. Thus, if the mashing calls for a typical "35 gallon mash," 35 gallons less 3.7 gallons or 31.3 gallons of water should be introduced for each 56 pounds of total grain, including malt. This close measurement of water is necessary and only possible because no other water, from any source, is used in the unique system of the invention. A truly remarkable aspect of this lies in the fact that all of the process water is present at both the time of the wetting of the grain as well as at the gelling temperature of the cooking.

The temperature of the water used for the wetting or make-up of the milled grain slurry in vessel 7 should be on the order of from between about 120° to 140° F. The source of the heated mashing water held in the storage tank 14 can be that of the discharge from a condenser and/or cooling water used to cool the mash (the cooked grain). In any event, a temperature of at least 120° F. will speed the wetting operation and reduce the BTU requirements of the cooking operation. (The mashing water will largely control the temperature of the slurry at the bottom of the cooker.) From the cooking or mashing standpoint, the higher the mashing water temperature, the lower the BTU requirement of the cooking. At high mash water temperatures, a balance between the BTU savings and possible increased enzymatic (non-malting) activity at temperatures of 135° F. to 140° F. or above must be maintained with temperatures above 140° F. not being preferred.

As discussed above, the grain is milled via the dicing and flaking rolls for proper wetting. This operation will also open up the grain structure and permit more rapid reactions of enzymes in the uncooked grain. Therefore, the time of the preparation of the slurry in the make-up vessel 7 is preferably kept as short as possible. Thus, the slurry mixing or "mingling" tank 7 should be sized to retain no more than the volume of flow for about 5 minutes. A retention time of about 2 to 3 minutes is preferred with this only requiring proper sizing of the vessel based on the intended or desired production. The slurry tank 7 is preferably equipped with an over-the-side mixer 8 that is sufficient to keep the slurry in violent agitation. This aids in the breaking-up of the flaked grain.

The slurry comprising the milled grain passes from the makeup tank 7 through a conduit 15 where it is pumped by way of positive displacement pump 16 into the inlet end of an electric cooker or mashing unit indicated generally at 17. The slurry pump 16 should comprise a variable speed positive displacement, solids handling pump capable of developing sufficient pressure so as to help in the forcing of the gelled mash through and from the cooking unit 17. Such pumps are commercially available.

With reference to FIG. 1, the cooking unit 17 includes an electrode 18 positioned within a cylindrical outer wall 19. As shown in the drawing, the electrode 18, outer wall 19, as well as the inlet feed conduit 20 may be mounted within and supported by the base or support member 21.

A suitable AC power supply across the central electrode 18 and the outer conductive wall 19 supply the necessary electrical power for heating the slurry. Inherent in this statement is the fact that the electrical path from the power supply (through the electrodes 18 and 19) is completed through the electrically conductive slurry. As will be appreciated by those skilled in the art, the optimum current density (amperes per square inch of electrode area) is a function of the dimensions of the cooking unit, the latter depending upon the temperature of the grain slurry and the flow rate required for plant production (i.e., bushel per day, gallons of mash per bushel, etc.). The current density is significant from the standpoint that if too much current (heat) is applied at any one point, the fluid heating will not be uniform and premature gelling may occur. Too high a current-density will gell the starch at the bottom of the cooker. Too low a current-density will not provide enough current to properly attain gelling at the top (discharge) of the cooker. In experiments and tests leading to the present invention, it has been discovered that a residence time (of the slurry in the cooker) of from between about 30 to 60 seconds and a current-density of less than about 4.0 amperes at 120 V. per square inch, or its electrical equivalent, e.g., 2.0 amps at 240 volts or 1 amp at 480 V., etc, of the central electrode are particularly advantageous and are thus preferred. A given production rate will thus set the dimensions of the cooker with units having a diameter on the order of about 6 inches and a length of about 2 feet being the optimum for present commercial use. Diameters larger than 6 inches may require excessive voltages. It should be recognized that a plurality or series of individual cooking or mashing units may be employed for high production distilleries. In this regard, FIG. 2 shows 3 cooking or mashing units operably connected to a conventional three-phase current. In this case, i.e., multiple cookers, the slurry may be delivered through a header or by individual pumps, one for each cooker.

The current supply may be any grounded single-phase industrial current. Should only three-phase current be available, and with reference to FIg. 2 the system may consist of three cookers, each on a phase (41) and each phase grounded (42). Each cooker is connected to a single-phase circuit with the grounded side of that circuit attached to the outer conductive shell (electrode 19). This specific arrangement for a single cooker or a series thereof as shown in FIG. 2 is required for the protection of both personnel and equipment.

In a system wherein a current is passed through an aqueous solution, it is unavoidable that some loss will occur. Thus, 100% of the energy applied cannot be recovered as measurable heat. Some of this loss can be attributed to electrolysis of water to hydrogen and oxygen. However, all of this is not lost in the practice of the present invention because the generation of small quantities of both hydrogen and oxygen within the heating fluid will provide an extremely effective disinfectant. This is stated inasmuch as it is an added benefit of electric cooking. During the development of the cooker characteristics, it was found that heat losses to electrolysis were very small and the heating efficiency of the experimental apparatus not including radiation losses was found to be close to 90%. That is, the observed heat delivery was 90% of the theoretical BTU of the power used.

As shown in the drawing, the cooking unit may include a power driven scraper or blade, indicated at 22, which rotates about the central electrode. The scraper keeps the gelled material moving and thus aids in the discahrge of the gell formed in the top of the cooker as well as serving to remove possible deposits from the central electrode 18 and outer shell or wall 19. The scraper must be of insulating or non-conductive material and arranged so that the least possible obstruction of the electrode area occurs. The outer wall 19 is preferably copper and should be insulated to prevent heat loss.

The gelled mass issues from the upper portion of the cooker 17 and is fed by way of an open chute or channel at the top of the cooker, indicated at 23, into a screw conveyor 24 wherein it is conveyed or passed to a pre-malting vessel 25. Approximately 10% of the total malt to be used in the system is introduced (from a malt storage tank 26) into the inlet end of the screw 24 along with the gelled mass. In this regard, since the discharge product of the cooker is a very heavy paste of mush, mechanically, it must be reduced to liquid form as quickly as possible. This may be done by using the aforesaid 10% of the total weight of malt to be used, in a pre-malting operation. Pre-malting may also be carried out by simply letting the cooker discharge fall into a tank or mixer 25 where ground malt may be added in the dry condition. Pre-malting will start hydrolysis of the starch properly and turn the mash into a viscous liquid in a matter of seconds at the discharge temperatures. Pre-malting may be accomplished at somewhat lower temperatures (±170° F.) by adding the dry malt in the retention tank 25 after the cooked mash has been collected from the cooker by a conveyor 24.

In all cases the pre-malt must be added to liquefy the mash. It is preferably done at high cook temperature to take advantage of the speed of the reaction.

The pre-malt holding tank 25 may be jacketed for cooling purposes but preferably it is maintained at above about 170° F., and with its contents being discharged through a cooler 27 capable of reducing the temperature of the mash to a range of between from about 140° to 160° F. The tank 25 should be equipped with agitation to keep the mash in motion.

The mash from the heat exchanger 27 is next passed to a vessel or tank 28 wherein the remainder of the process malt is added by way of conduit 29 connected to the ground storage tank 26 as shown in the drawing. The malted mash is retained in the malting tank 28 at about 145° F. before being further cooled to below about 90° F. prior to its introduction to the fermenter.

This main malting should be done in the holding tank 28 with about 40 to 45 minutes of flow retention. The main malt (90% of the total malt used) is added in the ground condition as a dry powder. The malting tank 28 should also be equipped with a mixer which will keep the initial bulk of retained mash in rapid motion. This tank is, of course, conventional and the size thereof is only a matter of proportioning to the flow rate.

The weight of malt to be used is that conventionally employed and, in general, should constitute from 11 to 14% of the total weight of grain used. Scaling (weighing) of the malt in the embodiment shown in the drawing is done on a continuous or traveling type scale — one for the pre-malt (30) and one for the main malt (31). Here, as with the original grain, bulk measuring may be used but it is not as accurate due to variations of the specific gravity of the ground material.

The further cooling of the malted mash, fermentation and recovery of the alcohol by distillation may be by any conventional and well-known techniques, the apparatus and operation of same being well known in the art. In the embodiment shown in the drawing, the malted mash is passed through a double pipe heat exchanger 32 as it is being pumped to the fermenter (not shown).

Yeasting may be done at any point after the mash has been cooled to below 90° F. In many processes, all of the yeast is added with the first mash in the fermenter. This permits yeast growth on the first mash delivered, providing more yeast bodies to succeeding quantities of mash coming to the fermenter.

However, and as stated above, yeasting and fermentation may be carried out in accordance with well established processes and equipment known in the art and they do not comprise a part of the present invention and its advantages and improved results except insofar as being part of the over-all combination of steps required in the production of the end product.

The following working examples will serve to better illustrate the invention but are expressly not intended to limit it thereto.

In a series of tests, the equipment employed was substantially the same as that shown in FIG. 1 except that the dicing and flaking rolls were not employed and the equipment and the cooker were bench scale set up in a laboratory. In these tests commercially ground whole wheat flour (having substantially the same wettability, size distribution and shape as diced and flaked corn kernals) was employed. Starch analysis of this flour was 67 to 68%. A 6 inches copper cooker one and one half inches in diameter and being plugged at one end with a rubber fitting having a central electrode and an annular opening for the introduction of the grain slurry (as substantially shown in FIG. 1) was used. Standard 120 V. current was used. The electrode length and spacing were such that a current draft of 7 amperes maximum was established. The current was applied by attaching the grounded side of the electrical system to the outside wall of the cooker and the "hot" terminal to the internal electrode.

A positive displacement pump, fed by gravity and discharging or feeding into the bottom of the cooker, was provided. The gelled mash was expelled from the top of the cooker and charged to a receiver. The system was capable of producing a gelled slurry at an operating rate of about 180 c.c. per minute when the grain was mixed with water at a temperature of about 140° F.

With no thermal insulation a 65° F. rise in temperature was obtained in 40 seconds of residence in the cooker. In the absence of pure culture yeast of specific strain, dried baker's yeast, obtainable on the retail shelf, was used. A weighed amount was added to the finished mash in the dry condition. Initial tests were run using a wine-maker's hydrometer as the method of determining alcohol percentage. An ebulliometer was used in subsequent tests.

Table 1 shows the remarkable results of a series of test obtained in accordance with this example with the alcohol percentages in these test being determined, after fermentation, with the ebulliometer.

The following is more detailed account of the test procedures used in this example.

Warm the pump motor and adjust speed to 60 strokes per minute, keep pump running.
Weigh 7.0 oz. wheat flour.
Weigh 1.0 oz. ground malt.
Measure 1 2/3 qts. water at 140° F.
Apply power to empty cooker.
Mix grain with water and transfer to the pump feed tank as quickly as possible.
As the slurry is pumped through the cooker, keep the feed tank stirred to keep the mix uniform, and stir the cooker to aid in discharge of the gelled mash.
When all of the mix has been drawn from the feed tank follow the slurry with 200 c.c. water to flush the cooker.
When cooking is complete, check temperature of mash and pre-malt with 2 grams (31 grains) of dry malt to liquefy. The temperature at this point should be 170 to 175° F.
Stir to cool to 140° F. and add remainder of 1.0 oz. of malt, as main-malt, dry.
Let stand with occasional stirring for 45 minutes and cool to 100° F.
Measure volume of finished mash.
Add 2 grams baker's yeast, dry.
Determine the following:
Specific gravity.
Brix.
Potential alcohol.
After 48 hours check:
Specific gravity.
Brix.
Potential alcohol.
Acidity (c.c. N/10 NaOH per 10 c.c. sample)
After 72 hours check:
Specific gravity.
Brix.
Potential alcohol (by hydrometer).
Percent alcohol (by ebulliometer).
After 96 hours check acidity only.

When repeated in still further test this method proved reproducible. It provided a cooked mash which was fairly stiff, and upon pre-malting produced a brown slurry which could be easily pumped, or would flow in standard piping. On the basis of using 0.5 pounds of grain and the indicated wash water, the procedure made an average of 1690 c.c. of mash. Converted to gallons of mash per 56 pound bushel of grain, this represents a "50 gallon mash". In these tests fermentation was complete in about 48 hours. An unexplained observation was that the electric cooking produced mashes of notable uniformity both for recorded data and the mode of fermentation.

The above and further experimental work and tests proved the preparing all the grain starch so that only gelled starch becomes the substrate for malt as per the practice of the invention does in act serve to increase the yield of alcohol from grain. The recorded results of a series of separate fermentations established and show:

1. That gelled mashes may be pre-malted for liquefying without interfering with the main hydrolysis of the starch by malt.
2. That grain can be fermented to close to the theoretical yield of alcohol by practicing the method of the invention.
3. That, if properly prepared, a grain of approximately 68% starch can be made to produce a yield of 5.65 to 5.80 proof gallons per bushel of 56 pounds.
4. That proper preparation of grain for distillery mashes is dependent upon elimination of exzymatic activity prior to the gelling of the starch, and presenting the highest possible quantity of gelled starch to the malt.

In accordance with further examples and tests and employing equipment substantially shown in FIG. 1, further grains including corn and rice were used as the source of the starch. The operating parameters, e.g., temperatures, etc., were those as discussed hereinabove. The results were substantially as shown in Table 1 with data from all tests clearly showing that grains can be fermented to close to the theoretical yield of alcohol when following the practice and teachings of the instant invention. The dicing rollers employed in these tests were 10 inches O.D. by 36 inches in length with the upper rollers having 7 cuts per inch and ¾ per foot spiral. The speed of the rollers were such that the upper roller was 2 times that of the lower. The lower roller had 7 cuts per inch with a single groove as a thread at 7 per inch. The flaking rollers were 15 inches O.D. by 30 inches in length. These rollers were hollow and water cooled. Both rolls and a polish finish and were run face to face and geared to drive at a speed ratio of 1:1.

TABLE I

| TEST NUMBER: | 1 | 2 | 3 | 4 | 5 | 6 |
|---|---|---|---|---|---|---|
| Line Voltage | 123 | 123 | 125 | 124 | 122 | 123 |
| Average Amperes | 6.0 | 6.4 | 5.0 | 5.0 | 5.0 | 5.0 |
| Cooking Time (Min.) | 6.0 | 6.0 | 8:40 | 7:45 | 8:30 | 8:35 |
| Power Draft (Watts) | 738 | 787 | 625 | 620 | 610 | 615 |
| Batch T. at Receiver (F) | 167 | 170 | 152 | 158 | 160 | 158 |
| Pre Malt T. | 158 | 153 | 148 | 154 | 152 | 150 |
| Main Malt T. | 140 | 140 | 140 | 140 | 140 | 140 |
| Finished Vol. c.c. | 1670 | 1635 | 1655 | 1670 | 1650 | 1633 |
| Gal. | 0.441 | 0.432 | 0.437 | 0.441 | 0.436 | 0.431 |
| Gal./Bu. | 49.4 | 48.3 | 49.0 | 49.3 | 48.7 | 48.3 |
| Sp. Gr. | 1.050 | 1.055 | 1.046 | 1.048 | 1.046 | 1.046 |
| 48 Hrs.: Sp. Gr. | 1.003 | 1.003 | 1.0005 | 1.003 | 1.003 | 1.001 |
| Acidity | 5.4 | 5.6 | 4.8 | 4.8 | 4.7 | 4.4 |
| 72 Hrs.: Sp. Gr. | 1.000 | 1.000 | 0.999 | 1.000 | 1.000 | 1.000 |

TABLE I-continued

| TEST NUMBER: | 1 | 2 | 3 | 4 | 5 | 6 |
|---|---|---|---|---|---|---|
| Acidity | 5.5 | 5.5 | 4.8 | 4.8 | 5.0 | 5.0 |
| Ebuliometer Ale % | 5.8 | 6.15 | 5.5 | 5.8 | 5.88 | 5.75 |
| Yield per 56 lb. Bu. | 5.72 | 5.85 | 5.38 | 5.72 | 5.74 | 5.55 |

Electrode Area = 2.94 Sq. Inches Cooker with Stirring Blade.
Grain = 7 ounces Whole Wheat Flour (Tests Nos. 3 and 4 - 67% Starch).
Water = 1-⅜ Qts. at 140° F + Wash out.
1 ounce Malt.
35 grains (2 oz.) Dry Yeast.

What is claimed is:

1. An apparatus for cooking a slurry of cereal grains and like starch materials, said apparatus having a central electrode positioned within an electrically conductive outer cylindrically shaped wall forming a heating chamber around said central electrode, said central electrode and outer cylindrical wall having first and second end portions respectively; support means positioned at the first ends of said central electrode and cylindrical outer wall for supporting same, said support means being formed of a non-conductive material; inlet means positioned near the first end of said outer cylindrical wall for introducing the slurry to be heated into said heating chamber formed by said central electrode and outer cylindrical wall; an AC power source connected across said central electrode and said outer conductive wall whereby the electrical path for said power source is completed through the said slurry to thereby cause said slurry to be heated and means positioned near the second end of said outer conductive wall for collecting and removing the heated slurry from said heating chamber.

2. The apparatus in accordance with claim 1, said apparatus further comprising a scraper blade rotatably mounted within said chamber formed by said central electrode and outer conductive cylindrical wall, said scraper blade serving, upon rotation thereof, to remove solid deposits from the surfaces of said electrode and outer wall.

3. The apparatus in accordance with claim 1, and further comprising pump means; said inlet means connected to said first end of said outer cylindrical wall being connected with said pump means for introducing said slurry into said heating chamber formed by said central electrode and said outer cylindrical wall, said pump means comprising a variable-speed positive-displacement slurry pump.

4. An apparatus for producing ethyl alcohol from cereal grains, said apparatus comprising; means for cutting and breaking certain grain into small fragments; means for continuously adding water at a temperature of about 120° to 140° F to the said grain fragments so as to form a water slurry thereof; a holding vessel for retaining said grain slurry; a cooking unit; means for passing said slurry into said cooking unit; said cooking unit having a central electrode positioned within an electrically conductive outer cylindrically shaped wall forming a chamber around said central electrode, said central electrode and outer cylindrical wall having first and second end portions respectively; support means positioned at the first ends of said central electrode and cylindrical outer wall for supporting same; a power source connected across said central electrode and said outer conductive wall whereby the electrical path for said power source is completed through the said slurry to thereby cause said slurry to be heated and means positioned near the second end of said outer conductive wall for collecting and removing the resulting gelled mash from said cooking unit.

* * * * *